United States Patent [19]
Tokura

[11] Patent Number: 5,495,424
[45] Date of Patent: Feb. 27, 1996

[54] METHOD AND APPARATUS FOR INSPECTING SOLDER PORTIONS

[75] Inventor: Nobufumi Tokura, Fukuoka, Japan

[73] Assignee: Matsushita Electric Industrial Co., Ltd., Osaka, Japan

[21] Appl. No.: 200,960

[22] Filed: Feb. 24, 1994

Related U.S. Application Data

[63] Continuation-in-part of Ser. No. 169,740, Dec. 20, 1993, abandoned, which is a continuation of Ser. No. 685,958, Apr. 17, 1991, abandoned.

[30] Foreign Application Priority Data

Apr. 18, 1990 [JP] Japan ................... 2-101979

[51] Int. Cl.⁶ .................................... G06F 17/00
[52] U.S. Cl. ................ 364/507; 364/525; 382/150; 348/129
[58] Field of Search ................... 364/552, 507, 364/525; 382/141, 144, 145, 146, 150; 348/86, 90, 92, 126, 129; 356/237; 324/538

[56] References Cited

U.S. PATENT DOCUMENTS

| | | | |
|---|---|---|---|
| 4,481,664 | 11/1984 | Linger et al. | 358/106 |
| 4,570,180 | 2/1986 | Baier et al. | 358/106 |
| 4,688,939 | 8/1987 | Ray | 356/237 |
| 4,758,782 | 7/1988 | Kobayashi | 382/8 |
| 4,772,125 | 9/1988 | Yoshimura | 358/106 |
| 4,928,313 | 5/1990 | Leonard et al. | 382/8 |
| 4,988,202 | 1/1991 | Nayar et al. | 356/237 |
| 5,023,916 | 6/1991 | Breu | 358/106 |
| 5,064,291 | 11/1991 | Reiser | 358/106 |
| 5,103,105 | 4/1992 | Ikegaya et al. | 356/237 |
| 5,148,375 | 9/1992 | Horirami | 364/552 |

OTHER PUBLICATIONS

Seminar Text "New Image Processing Technique for Remarkably Changing Visual Inspection Process", Society of Engineers of Precision Engineering, pp. 38–46, Jan. 26, 1989.

"Digital Image Processing", by Gonzalez et al, Addison–Wesely Publishing Co., Massachusetts, USA, pp. 118–136 and 320–325, 1977.

"Computer Vision", by Ballard et al, Prentice–Hall, Inc., New Jersey, USA, pp. 352–382, 1982.

*Primary Examiner*—Ellis B. Ramirez
*Attorney, Agent, or Firm*—Lowe, Price, LeBlanc & Becker

[57] ABSTRACT

A solder portion is inspected as follows. An image of the solder portion is obtained. The image of the solder portion is collated with a plurality of predetermined reference patterns corresponding to different solder portion types respectively. A type of the solder portion is identified in response to a result of the collation. A decision is made as to whether the solder portion is satisfactory or unsatisfactory in response to the identified type thereof.

8 Claims, 8 Drawing Sheets

FIG. 4
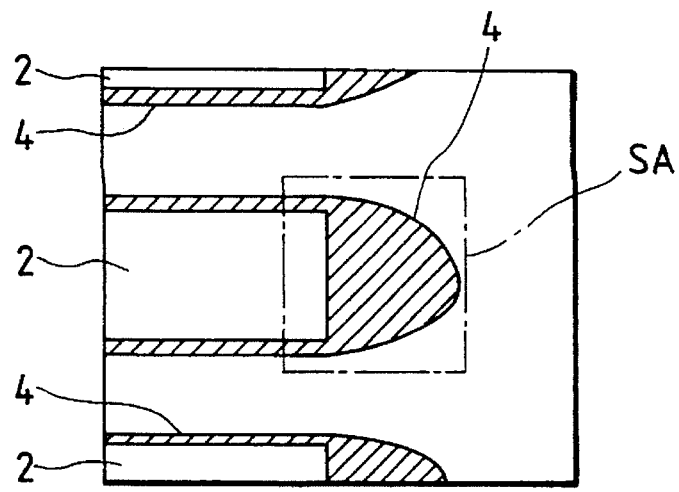
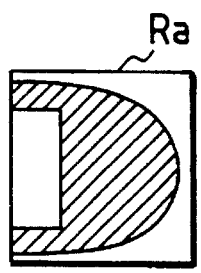
FIG. 5
Ra
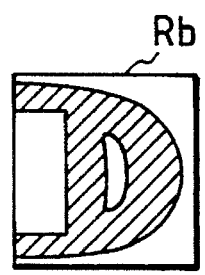
FIG. 6
Rb
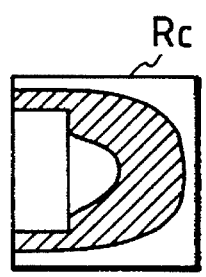
FIG. 7
Rc
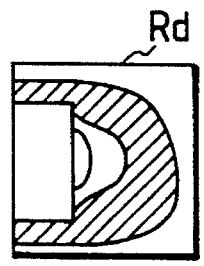
FIG. 8
Rd
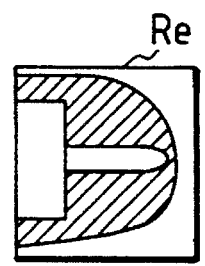
FIG. 9
Re
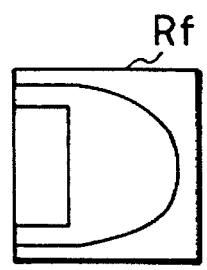
FIG. 10
Rf

METHOD AND APPARATUS FOR INSPECTING SOLDER PORTIONS

CROSS-REFERENCES TO RELATED APPLICATIONS

This is a continuation-in-part of U.S. patent application Ser. No. 169,740, filed on Dec. 20, 1993, which is a continuation of U.S. patent application Ser. No. 685,958, filed on Apr. 17, 1991 now abandoned.

BACKGROUND OF THE INVENTION

1. Field of the Invention

This invention relates to a method and an apparatus for inspecting solder portions on, for example, a printed circuit board.

2. Description of the Prior Art

U.S. Pat. No. 5,023,916 discloses a method of inspecting solder joints that connect surface-mount electronic components to printed circuit boards. The method of U.S. Pat. No. 5,023,916 includes the steps of obtaining an image of a plurality of the leads of the electronic component, representing segments of the image that correspond to each of the leads by polygons, projecting each of pixel intensity values within each polygon onto an axial dimension to provide a measured waveform, comparing the measured waveform for each lead with a corresponding model waveform, and classifying each lead as being either satisfactory or unsatisfactory on the basis of the comparisons.

SUMMARY OF THE INVENTION

It is an object of this invention to provide an improved method of inspecting a solder portion on, for example, a printed circuit board.

It is another object of this invention to provide an improved apparatus for inspecting a solder portion on, for example, a printed circuit board.

A first aspect of this invention provides a method of inspecting a solder portion which comprises the steps of obtaining an image of the solder portion; collating the image of the solder portion with a plurality of predetermined reference patterns corresponding to different solder portion types respectively; identifying a type of the solder portion In response to a result of the collating step; and deciding whether the solder portion is satisfactory or unsatisfactory in response to the identified type thereof.

A second aspect of this invention provides a method of inspecting a solder portion which comprises the steps of obtaining an image of the solder portion; calculating rates of matching of the image of the solder portion with predetermined reference patterns corresponding to different solder portion types respectively; selecting a maximum matching rate from among the calculated matching rates; comparing the maximum matching rate with a predetermined reference matching rate; identifying a type of the solder portion as being equal to the type corresponding to the maximum matching rate when the maximum matching rate is greater than the reference matching rate; and deciding whether the solder portion is satisfactory or unsatisfactory in response to the identified type thereof.

A third aspect of this invention provides an apparatus for inspecting a solder portion which comprises means for obtaining an image of the solder portion; means for collating the image of the solder portion with a plurality of predetermined reference patterns corresponding to different solder portion types respectively; means for identifying a type of the solder portion in response to a result of the collating by the collating means; and means for deciding whether the solder portion is satisfactory or unsatisfactory in response to the identified type thereof.

A fourth aspect of this invention provides a method of inspecting a solder portion which comprises the steps of obtaining an image of the solder portion; deciding which of predetermined reference patterns corresponding to different solder portion types respectively is most similar to the image of the solder portion, wherein each of the reference patterns corresponds to either a satisfactory solder portion state or an unsatisfactory solder portion state; identifying a type of the solder portion as being equal to the type corresponding to the reference pattern most similar to the image of the solder pattern; and deciding whether the solder portion is satisfactory or unsatisfactory in response to the identified type thereof.

A fifth aspect of this invention provides an apparatus for inspecting a solder portion which comprises means for obtaining an image of the solder portion; means for deciding which of predetermined reference patterns corresponding to different solder portion types respectively is most similar to the image of the solder portion, wherein each of the reference patterns corresponds to either a satisfactory solder portion state or an unsatisfactory solder portion state; means for identifying a type of the solder portion as being equal to the type corresponding to the reference pattern most similar to the image of the solder pattern; and means for deciding whether the solder portion is satisfactory or unsatisfactory in response to the identified type thereof.

BRIEF DESCRIPTION OF THE DRAWINGS

FIG. 4 is a diagram of an example of an image of a solder portion which is obtained by the apparatus in FIG. 1.

FIG. 5 is a diagram of a first reference pattern.

FIG. 6 is a diagram of a second reference pattern.

FIG. 7 is a diagram of a third reference pattern.

FIG. 8 is a diagram of a fourth reference pattern.

FIG. 9 is a diagram of a fifth reference pattern.

FIG. 10 is a diagram of a sixth reference pattern.

DESCRIPTION OF THE PREFERRED EMBODIMENT

Figure 1:
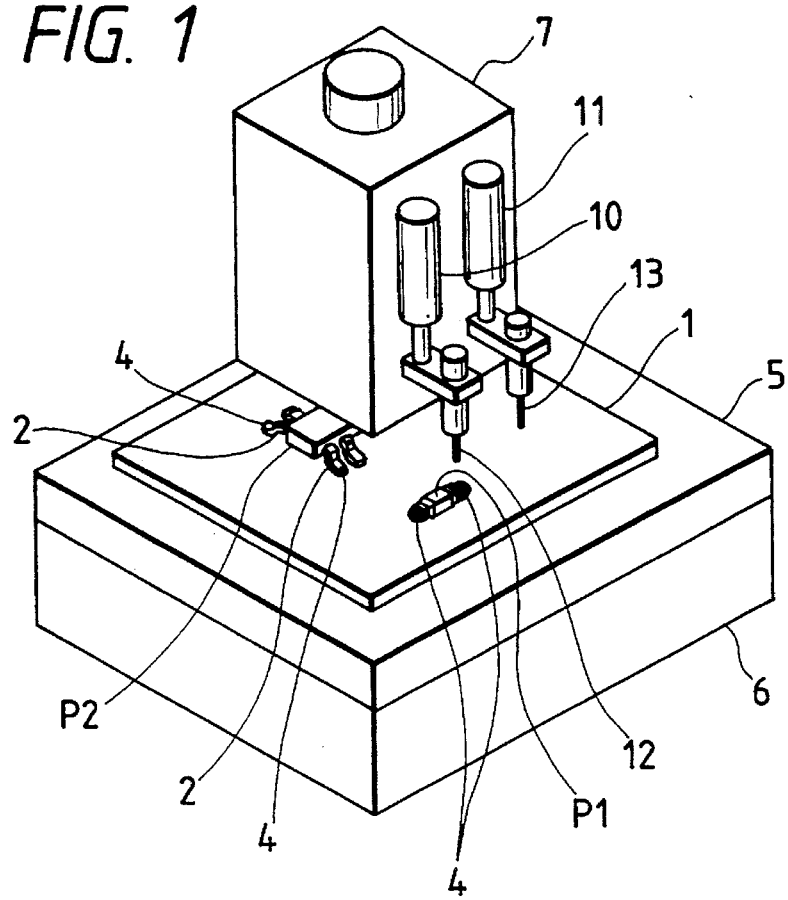
FIG. 1 is a perspective view of an apparatus for inspecting solder portions according to an embodiment of this invention.

With reference to FIG. 1, electronic components or parts including a rectangular parallelepiped electronic component P1 and a lead-equipped electronic component P2 are mounted on a printed circuit board 1 by solder portions 4. The electronic component P2 has a plurality of leads 2.

The printed circuit board 1 is retained by a holder 5 attached to a horizontally-movable table 6 generally referred to as an XY table 6. The table 6 can move in two directions perpendicular to each other, that is, X and Y directions, on a horizontal plane. The table 6 can be driven by actuators 6A (not shown in FIG. 1, see FIG. 3). The printed circuit board 1 moves horizontally together with the table 6.

Figure 2:
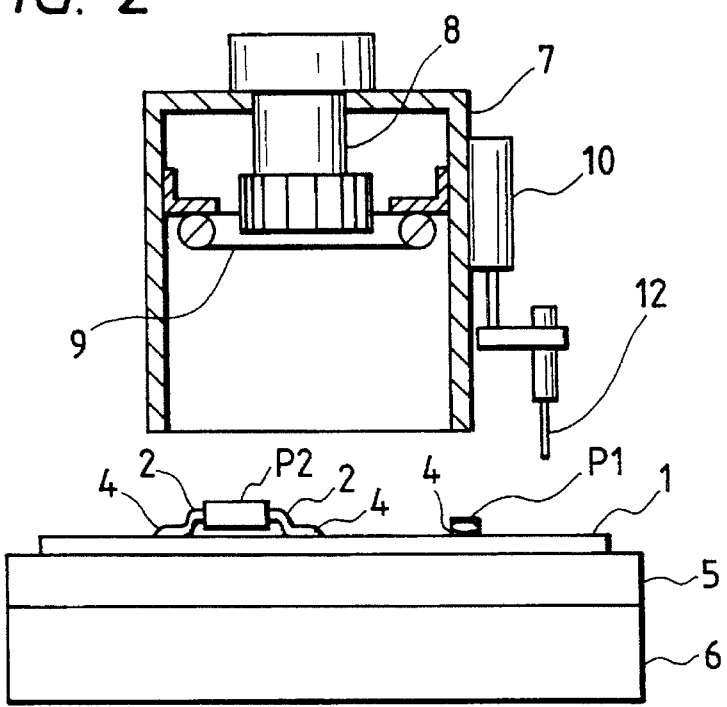
FIG. 2 is a sectional view of the apparatus in FIG. 1.

A casing 7 fixed by a suitable support (not shown) is located above the printed circuit board 1. As shown in FIG. 2, a camera 8 and a ring-shaped light source 9 are fixed within the casing 7 by suitable members. The light source 9 may include an array of LED's. The casing 7 has a lower opening via which light from the light source 9 is applied to the printed circuit board 1 to illuminate the latter. The camera 8 converts an image of the printed circuit board 1 into a corresponding electric image signal. The image of the printed circuit board 1 includes images of the solder portions 4.

As shown in FIGS. 1 and 2, the bodies of cylinder actuators (simply referred to as cylinders) 10 and 11 are attached to a side of the casing 7. The cylinders 10 and 11 have vertically-movable rods, the lower ends of which hold markers 12 and 13 respectively. The marker 12 is used in putting a red mark on a region of the printed circuit board 1 near a solder portion 4 which is decided to be no good (NG). The marker 13 is used in putting a yellow mark on a region of the printed circuit board 1 near a solder portion 4 which is decided to be gray (GRAY) intermediate between good (all correct, OK) and no good (NG). Putting red and yellow marks on the printed circuit board 1 is executed by activating the cylinders 10 and 11 and lowering their rods into contact with an upper surface of the printed circuit board 1.

Figure 3:
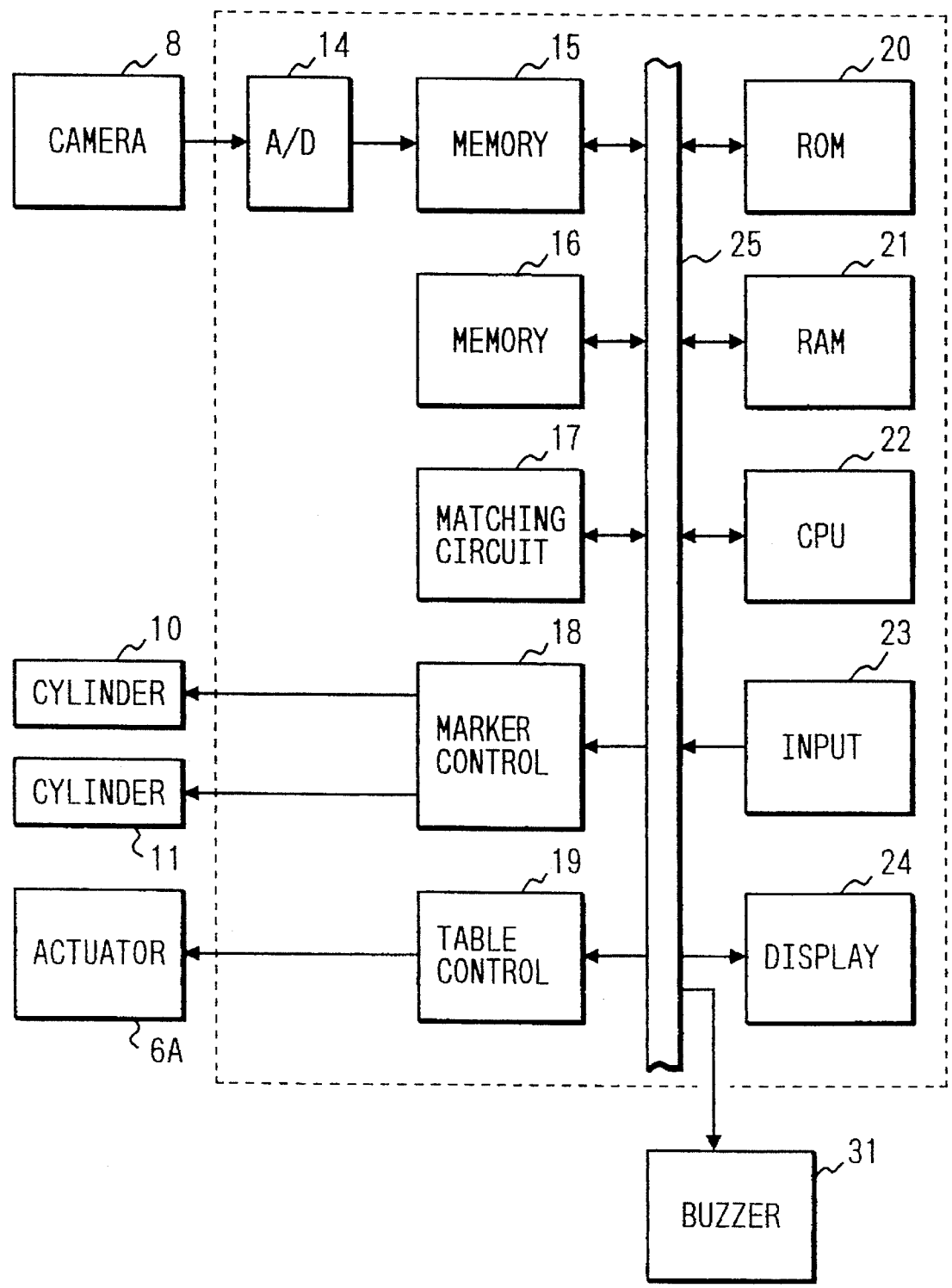
FIG. 3 is a block diagram of the apparatus in FIG. 1.

With reference to FIG. 3, the electric image signal outputted from the camera 8 is converted into a corresponding digital image signal by an A/D converter 14. The digital image signal outputted from the A/D converter 14 is stored into a first memory 15. FIG. 4 shows an example of an image represented by the digital image signal stored in the first memory 15. The image in FIG. 4 includes images of leads 2 and solder portions 4. It should be noted that the image represented by the digital image signal stored in the first memory 15 is of a gray scale type (a multiple-tone or halftone type) in fact but the image in FIG. 4 is illustrated as a bi-tone image (a black-white image) for the simplicity of illustration.

A second memory 16 stores digital signals representing predetermined reference images or predetermined reference patterns Ra, Rb, Rc, Rd, Re, and Rf. FIG. 5, FIG. 6, FIG. 7, FIG. 8, FIG. 9, and FIG. 10 show examples of the reference patterns Ra, Rb, Rc, Rd, Re, and Rf respectively. The reference patterns Ra, Rb, Rc, Rd, Re, and Rf correspond to images of typical solder portions respectively. It should be noted that each of the reference patterns Ra, Rb, Rc, Re, and Rf is of a gray scale type (a multiple-tone or halftone type) in fact but the image in each of FIG. 5, FIG. 6, FIG. 7, FIG. 9, and FIG. 10 is illustrated as a bi-tone image (a black-white image) for the simplicity of illustration.

A pattern matching circuit 17 including a calculator serves to execute matching between an image segment in a search area "SA" (see FIG. 4) represented by the digital image signal in the first memory 15 and each of the reference patterns Ra–Rf represented by the digital signals in the second memory 16. Specifically, the pattern matching circuit 17 calculates matching rates Ma, Mb, Mc, Md, Me, and Mf. The rate Ma relates to matching between the image segment in the search area "SA" represented by the digital image signal in the first memory 15 and the reference pattern Ra represented by the digital signal in the second memory 16. The rate Mb relates to matching between the image segment in the search area "SA" represented by the digital image signal in the first memory 15 and the reference pattern Rb represented by the digital signal in the second memory 16. The rate Mc relates to matching between the image segment in the search area "SA" represented by the digital image signal in the first memory 15 and the reference pattern Rc represented by the digital signal in the second memory 16. The rate Md relates to matching between the image segment in the search area "SA" represented by the digital image signal in the first memory 15 and the reference pattern Rd represented by the digital signal in the second memory 16. The rate Me relates to matching between the image segment in the search area "SA" represented by the digital image signal in the first memory 15 and the reference pattern Re represented by the digital signal in the second memory 16. The rate Mf relates to matching between the image segment in the search area "SA" represented by the digital image signal in the first memory 15 and the reference pattern Rf represented by the digital signal in the second memory 16.

Each of the calculated matching rates Ma–Mf depends on the degree of the similarity between the image segment in the search area "SA" represented by the digital image signal in the first memory 15 and the reference pattern represented by the digital signal in the second memory 16. Specifically, each of the calculated matching rates Ma–Mf increases in accordance with an increase in the degree of the similarity between the image segment in the search area "SA" represented by the digital image signal in the first memory 15 and the reference pattern represented by the digital signal in the second memory 16.

Figure 31:
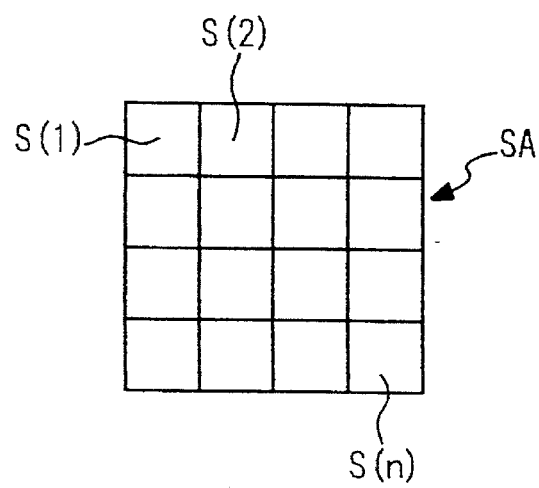
FIG. 31 is a diagram of a matrix array of pixels composing an image segment in a search area.
Figure 32:
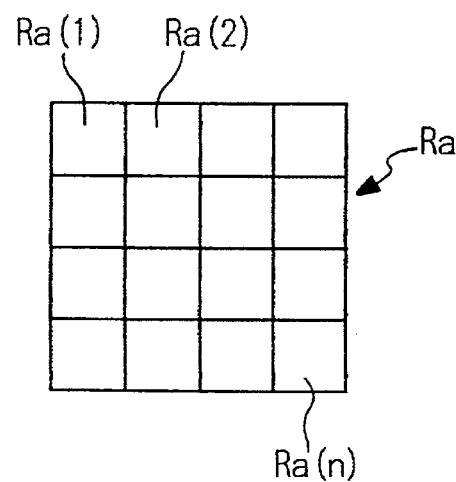
FIG. 32 is a diagram of a matrix array of pixels composing a reference pattern.

A further description will now be given of the pattern matching circuit 17. As shown in FIG. 31, the image segment in the search area "SA" represented by the digital image signal in the first memory 15 is composed of a matrix array of N by N pixels, where "N" denotes a predetermined natural number (equal to, for example, 4) and "n" denotes a predetermined natural number equal to $N^2$. In addition, the digital image signal in the first memory 15 which represents the image segment in the search area "A" is divided into segments corresponding to the pixels respectively. The pixel-corresponding segments of the digital image signal in the first memory 15 represent tone values or luminance values $S(1), S(2), \ldots,$ and $S(n)$ at the pixels respectively. As shown in FIG. 32, the reference pattern Ra represented by the digital signal in the second memory 16 is composed of a matrix array of N by N pixels. In addition, the digital signal in the second memory 16 which represents the reference pattern Ra is divided into segments corresponding to the pixels respectively. The pixel-corresponding segments of the digital signal of the reference pattern Ra represent tone values or luminance values $Ra(1), Ra(2), \ldots,$ and $Ra(n)$ at the pixels respectively. The pattern matching circuit 17 includes a calculator, a programmable calculator, or a similar device. First, the pattern matching circuit 17 calculates parameters Srs, Srr, and Sss from the pixel tone values $S(1), S(2), \ldots,$ and $S(n)$ and the pixel tone values $Ra(1), Ra(2), \ldots,$ and $Ra(n)$ according to the following equations.

$$Srs = \sum_{i=1}^{n} \sum_{j=1}^{n} Ra(i) \cdot S(j) - \frac{1}{n} \cdot \left\{ \sum_{i=1}^{n} Ra(i) \cdot \sum_{j=1}^{n} S(j) \right\}$$

$$Srr = \sum_{i=1}^{n} \{Ra(i)\}^2 - \frac{1}{n} \cdot \left\{ \sum_{i=1}^{n} Ra(i) \right\}^2$$

$$Sss = \sum_{j=1}^{n} \{S(j)\}^2 - \frac{1}{n} \cdot \left\{ \sum_{j=1}^{n} S(j) \right\}^2$$

Then, the pattern matching circuit 17 calculates the matching rate Ma from the parameters Srs, Srr, and Sss by referring to the following equation.

$$Ma = \frac{Srs^2}{Srr \cdot Sss}$$

Each of the other reference patterns Rb–Rf represented by the digital signals in the second memory 16 is composed of a matrix array of N by N pixels. In addition, each of the digital signals in the second memory 16 which represent the reference patterns Rb–Rf is divided into segments corresponding to the pixels respectively. The pixel-corresponding segments of the digital signals of the reference patterns Rb–Rf represent tone values or luminance values at the pixels respectively. The pattern matching circuit 17 calculates the other matching ratios Mb, Mc, Md, Me, and Mf similarly to the previously-mentioned calculation of the matching ratio Ma.

A marker controller 18 including a drive circuit serves to control the cylinders 10 and 11 for actuating the markers 12 and 13. A table controller 19 including a drive circuit serves to control the actuators 6A for the table 6. A ROM 20 stores programs and other information. A RAM 21 serves to store digital signals. A CPU 22 operates in accordance with a program stored in the ROM 20. An input portion 23 including a keyboard is used in inputting data or signals. A display portion 24 including a CRT serves to indicate images and information of various types. A buzzer 31 serves to generate sound. The first memory 15, the second memory 16, the pattern matching circuit 17, the marker controller 18, the table controller 19, the ROM 20, the RAM 21, the CPU 22, the input portion 23, the display portion 24, and the buzzer 31 are connected to each other via a bus 25.

Figure 11:
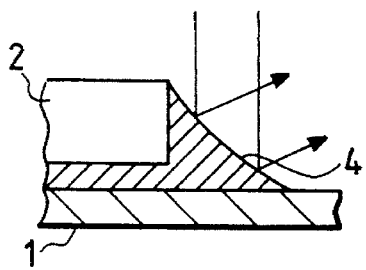
FIG. 11 is a sectional view of a solder portion of a first type.
Figure 12:
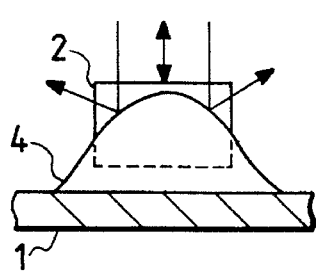
FIG. 12 is a front view of the solder portion in FIG. 11.
Figure 13:
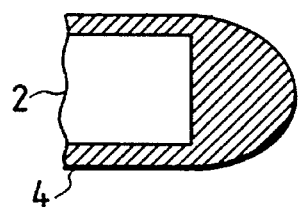
FIG. 13 is a diagram of an image of the solder portion in FIG. 11.

FIGS. 11, 12, and 13 show a solder portion 4 of a type "A". As shown in FIG. 11, the solder portion 4 of the type "A" is adequately adapted to a lead 2 with a good wettability, and therefore has a triangular section. As shown in FIG. 12, the solder portion 4 of the type "A" has a front side configuration similar to the shape of a knoll. Most of the light applied to the surfaces of the solder portion 4 of the type "A" from the light source 9 is reflected toward inclined directions significantly deviating from the vertical upward direction so that it does not enter the camera 8. Therefore, as shown in FIG. 13, the solder portion 4 of the type "A" forms a dark area in the image obtained via the camera 8. On the other hand, the lead 2 forms a bright area in the image obtained via the camera 8 since the lead 2 has a flat upper surface.

Figure 14:
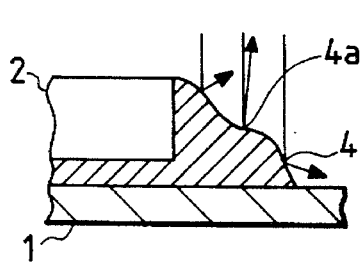
FIG. 14 is a sectional view of a solder portion of a second type.
Figure 15:
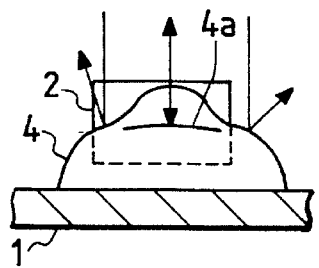
FIG. 15 is a front view of the solder portion in FIG. 14.
Figure 16:
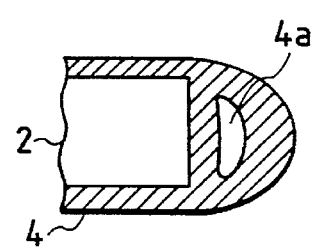
FIG. 16 is a diagram of an image of the solder portion in FIG. 14.

FIGS. 14, 15, and 16 show a solder portion 4 of a type "B". As shown in FIGS. 14 and 15, the solder portion 4 of the type "B" has a two-stage or two-step configuration. A horizontal flat area 4a extends in and around a center of the solder portion 4 of the type "B". Most of the light applied to the flat area 4a from the light source 9 is reflected toward the vertical upward direction so that it enters the camera 8. Therefore, as shown in FIG. 16, the flat area 4a forms a semicircular bright area in the image obtained via the camera 8. On the other hand, the solder portion 4 of the type "B" except the flat area 4a forms a dark area in the image obtained via the camera 8. The bright area corresponding to the flat area 4a extends within the dark area corresponding to the rest of the solder portion 4 of the type "B".

Figure 17:
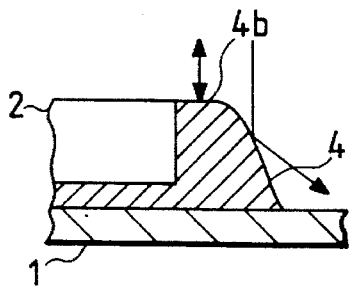
FIG. 17 is a sectional view of a solder portion of a third type.
Figure 18:
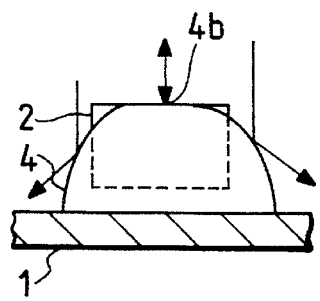
FIG. 18 is a front view of the solder portion in FIG. 17.
Figure 19:
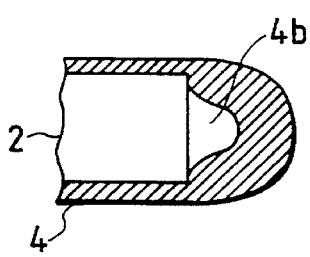
FIG. 19 is a diagram of an image of the solder portion in FIG. 17.

FIGS. 17, 18, and 19 show a solder portion 4 of a type "C". As shown in FIGS. 17 and 18, a horizontal flat area 4b extending from and being flush with an upper surface of a lead 2 lies at a top of the solder portion 4 of the type "C". Most of the light applied to the flat area 4b from the light source 9 is reflected toward the vertical upward direction so that it enters the camera 8. Therefore, as shown In FIG. 19, the flat area 4a forms a bright area in the image obtained via the camera 8. On the other hand, the solder portion 4 of the type "C" except the flat area 4b forms a dark area in the image obtained via the camera 8. The bright area corresponding to the flat area 4b extends from a bright area corresponding to the upper surface of the lead 2.

Figure 20:
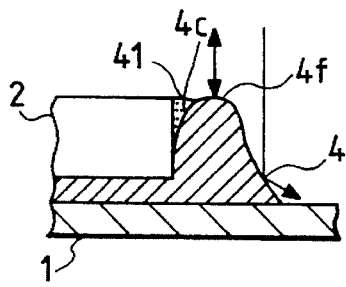
FIG. 20 is a sectional view of a solder portion of a fourth type.
Figure 21:
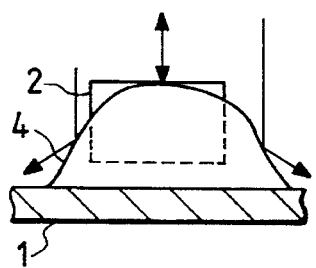
FIG. 21 is a front view of the solder portion in FIG. 20.
Figure 22:
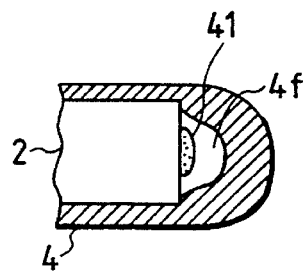
FIG. 22 is a diagram of an image of the solder portion in FIG. 20.

FIGS. 20, 21, and 22 show a solder portion 4 of a type "D". As shown in FIG. 20, the solder portion 4 of the type "D" is inadequately adapted to a lead 2 with a poor wettability so that a valley or recess 4c extends between the solder portion 4 and the lead 2. Flux 41 which has been used during a soldering process remains in the recess 4c. As shown in FIGS. 20 and 21, a horizontal flat area 4f lies at a top of the solder portion 4 of the type "D". As shown in FIG. 21, the solder portion 4 of the type "D" has a front side configuration basically similar to the shape of a knoll. A part of the light applied to the flux 41 in the recess 4c from the light source 9 is reflected toward the vertical upward direction so that it enters the camera 8. Therefore, as shown in FIG. 22, the flux 41 in the recess 4c forms a gray area in the image obtained via the camera 8. Most of the light applied to the flat area 4f from the light source 9 is reflected toward the vertical upward direction so that it enters the camera 8. Therefore, as shown in FIG. 22, the flat area 4f forms a bright area in the image obtained via the camera 8. On the other hand, the solder portion 4 of the type "D" except the recess 4c and the flat area 4f forms a dark area in the image obtained via the camera 8. The gray area corresponding to the flux 41 in the recess 4c extends between the bright area corresponding to the flat area 4f and a bright area corresponding to an upper surface of the lead 2. It should be noted that the luminance of the gray area exists between the luminance of the dark area and the luminance of the bright area.

Figure 23:
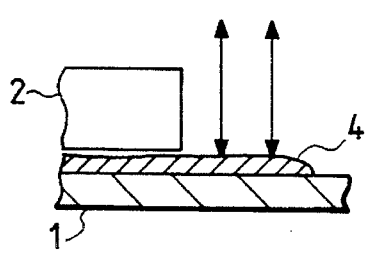
FIG. 23 is a sectional view of a solder portion of a fifth type.
Figure 24:
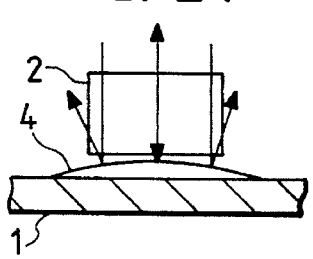
FIG. 24 is a front view of the solder portion in FIG. 23.
Figure 25:
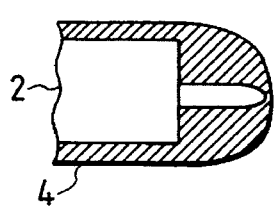
FIG. 25 is a diagram of an image of the solder portion in FIG. 23.

FIGS. 23, 24, and 25 show a solder portion 4 of a type "E". As shown in FIGS. 23 and 24, the solder portion 4 of the type "E" is not bonded to a lead 2. As shown in FIG. 25, the solder portion 4 of the type "E" has a front side configuration basically similar to the shape of a low hill or knoll. A top of the solder portion 4 of the type "E" is approximately flat, and is elongated along a horizontal plane. Most of the light applied to the top of the solder portion 4 of the type "E" from the light source 9 is reflected toward the vertical upward direction so that it enters the camera 8. Therefore, as shown in FIG. 25, the top of the solder portion 4 of the type "E" forms an elongated bright area in the image obtained via the camera 8. On the other hand, the solder portion 4 of the type "E" except the top thereof forms a dark area in the image obtained via the camera 8.

Figure 26:
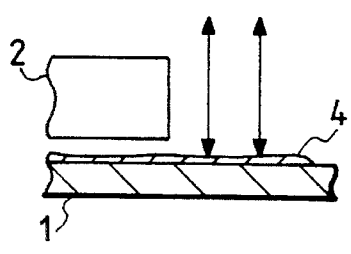
FIG. 26 is a sectional view of a solder portion of a sixth type.
Figure 27:
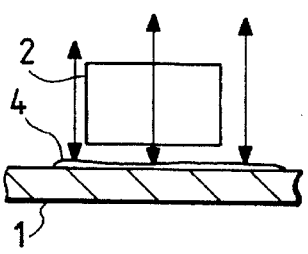
FIG. 27 is a front view of the solder portion in FIG. 26.
Figure 28:
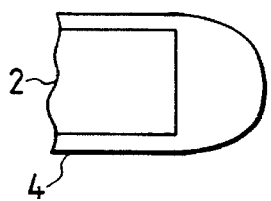
FIG. 28 is a diagram of an image of the solder portion in FIG. 26.

FIGS. 26, 27, and 28 show a solder portion 4 of a type "F". As shown in FIGS. 26 and 27, the solder portion 4 of the type "F" is not bonded to a lead 2. As shown in FIGS. 26 and 27, the solder portion 4 of the type "F" has a shape of a flat layer. Most of the light applied to the solder portion 4 of the type "F" from the light source 9 is reflected toward the vertical upward direction so that it enters the camera 8. Therefore, as shown in FIG. 28, the solder portion 4 of the type "F" forms a bright area in the image obtained via the camera 8. The bright area corresponding to the solder portion 4 of the type "F" extends from a bright area corresponding to an upper surface of the lead 2.

The solder portions 4 of the types "A", "B", and "C" are adequately bonded to the leads 2. Thus, the solder portions 4 of the types "A", "B", and "C" are satisfactory or good (all correct, OK). On the other hand, the solder portions 4 of the types "D", "E", and "F" are inadequately bonded to or fail to be bonded to the leads 2. Thus, the solder portions 4 of the types "D", "E", and "F" are unsatisfactory or no good (NG). The solder portions 4 of the types "A", "B", "C", "D", "E", and "F" correspond to respective typical solder portions which actually occur. The reference patterns Ra, Rb, Rc, Rd, Re, and Rf in FIGS. 5, 6, 7, 8, 9, and 10 are predetermined so as to agree with the solder portions 4 of the types "A", "B", "C", "D", "E", and "F" respectively. Accordingly, the reference patterns Ra, Rb, and Rc correspond to satisfactory solder portions (good solder portions or OK solder portions) while the reference patterns Rd, Re, and Rf correspond to unsatisfactory solder portions (poor solder portions or NG solder portions).

A preliminary process is executed before an actual inspection process. During the preliminary process, the reference patterns Ra, Rb, Rc, Rd, Re, and Rf are prepared and are registered in the second memory 16.

A detailed description will now be given of the preliminary process. During the preliminary process, a sample printed circuit board 1 having a typical solder portion 4 of the type "A" is placed on the holder 5. The table controller 19 is controlled by the CPU 22 in response to predetermined information of the position of the solder portion 4 of the type "A" so that the actuators 6A for the table 6 are driven to locate the solder portion 4 of the type "A" at a place directly below the camera 8. It should be noted that the information of the position of the solder portion 4 of the type "A" is previously stored in the ROM 20 or the RAM 21. The camera 8 converts an image of the printed circuit board 1 into a corresponding electric image signal while the printed circuit board 1 is illuminated by the light source 9. The image of the printed circuit board 1 includes an image of the solder portion 4 of the type "A". The electric image signal outputted from the camera 8 is converted into a corresponding digital image signal by the A/D converter 14. The digital image signal outputted from the A/D converter 14 is stored into the first memory 15. The CPU 22 reads out a portion of the digital image signal from the first memory 15 which represents an image segment in a search area "SA" (see FIG. 4). The CPU 22 stores the readout portion of the digital image signal into the second memory 16 as an indication of the reference pattern Ra. In this way, the reference pattern Ra is prepared and is registered in the second memory 16. Subsequently, the above-mentioned sequence of steps is executed for each of printed circuit boards having typical solder portions 4 of the types "B", "C", "D", "E", and "F" respectively. As a result, the reference patterns Rb, Rc, Rd, Re, and Rf are prepared and are registered in the second memory 16.

It should be noted that the reference patterns Ra, Rb, Rc, Rd, Re, and Rf may use artificial or pseudo patterns in which distributions of luminance are represented as mosaics.

Figure 29:
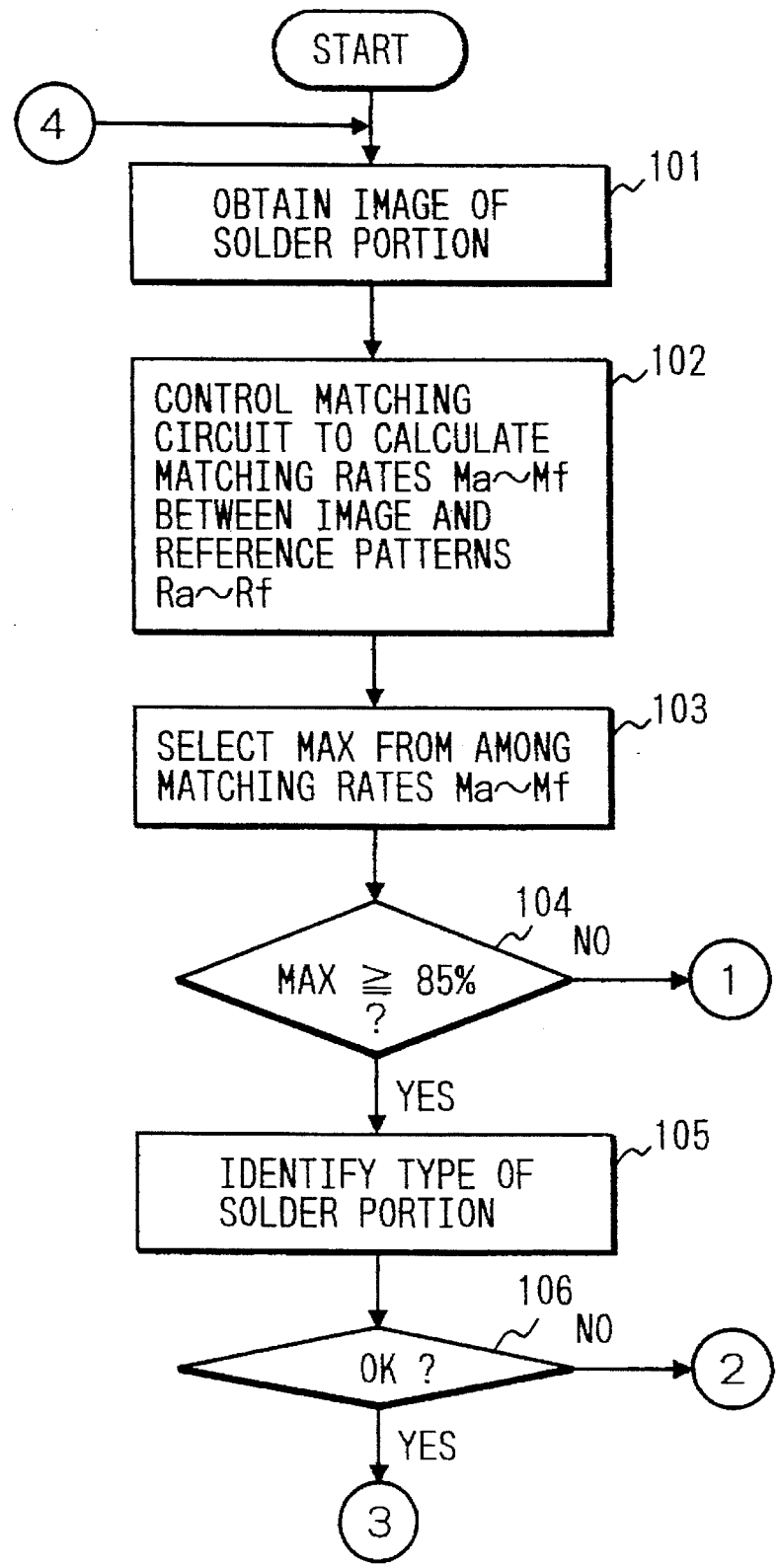
FIG. 29 and FIG. 30 are a flowchart of an inspection program for controlling a CPU in FIG. 3.
Figure 30:
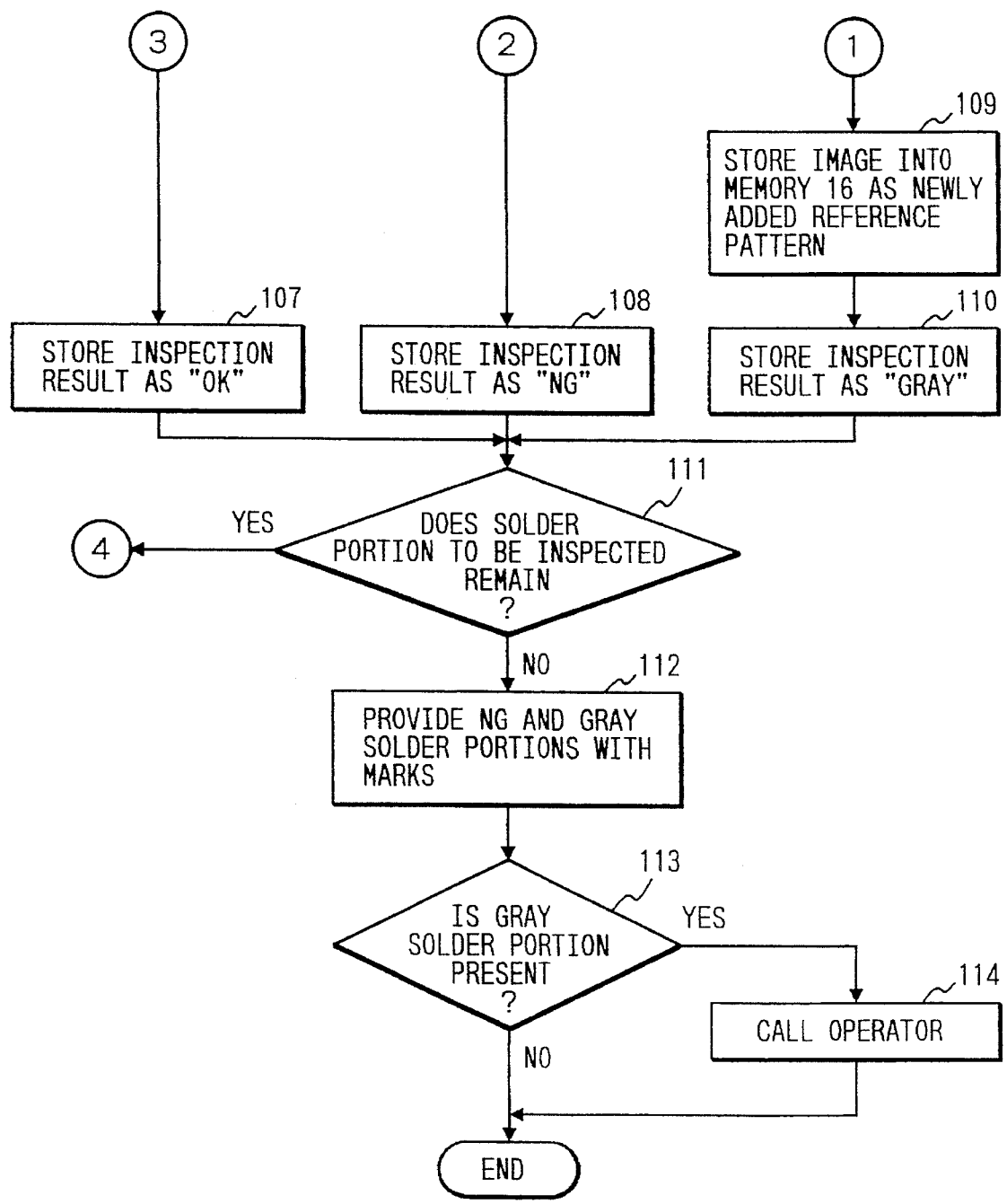

The preliminary process is followed by an actual inspection process. The actual inspection process will be described hereinafter in connection with operation of the CPU 22. As previously described, the CPU 22 operates in accordance with an inspection program stored in the ROM 20. FIGS. 29 and 30 are a flowchart of this program.

As shown in FIG. 29, a first step 101 of the program controls the table controller 19 in response to predetermined information of positions of solder portions 4 so that the actuators 6A for the table 6 are driven to locate first one of the solder portions 4 of a printed circuit board 1 at a place directly below the camera 8. It should be noted that the information of the positions of the solder portions 4 is previously stored in the ROM 20 or the RAM 21. The camera 8 converts an image of the printed circuit board 1 into a corresponding electric image signal while the printed circuit board 1 is illuminated by the light source 9. The image of the printed circuit board 1 includes an image of the first solder portion 4. The electric image signal outputted from the camera 8 is converted into a corresponding digital image signal by the A/D converter 14. The step 101 controls the first memory 15 so that the digital image signal outputted from the A/D converter 14 is stored into the first memory 15. FIG. 4 shows an example of an image represented by the digital image signal stored in the first memory 15. The image in FIG. 4 includes an image of the first solder portion 4 and an image of a related lead 2.

A step 102 following the step 101 reads out a portion of the digital image signal from the first memory 15 which represents an image segment in a search area "SA" (see FIG. 4). The image segment in the search area "SA" includes the image of the first solder portion 4 and the image of the related lead 2. The step 102 transfers the readout portion of the digital image signal from the first memory 15 to the pattern matching circuit 17. The step 102 sequentially transfers the digital signals representative of the reference images Ra, Rb, Rc, Rd, Re, and Rf from the second memory 16 to the pattern matching circuit 17. The step 102 controls the pattern matching circuit 17 so that the pattern matching circuit 17 collates the image segment in the search area "SA" with the reference images Ra, Rb, Rc, Rd, Re, and Rf, and calculates the matching rates Ma, Mb, Mc, Md, Me, and Mf.

A step 103 following the step 102 receives output signals of the pattern matching circuit 17 which represent the calculated matching rates Ma, Mb, Mc, Md, Me, and Mf. The step 103 detects and selects a maximum matching rate from among the matching rates Ma, Mb, Mc, Md, Me, and Mf.

A step 104 following the step 103 decides whether the maximum matching rate is equal to 85% or more. When the maximum matching rate is decided to be equal to 85% or more, the program advances from the step 104 to a step 105. Otherwise, the program advances from the step 104 to a step 109 of FIG. 30.

The step 105 decides the image segment in the search area "SA" to be of the same type as the reference pattern corresponding to the maximum matching rate. In other words, the step 105 decides which of the types "A", "B", "C", "D", "E", and "F" agrees with the type of the image segment in the search area "SA". In this way, the step 105 identifies the type of the image segment in the search area "SA".

A step 106 following the step 105 decides whether or not the first solder portion 4 is good (all correct, OK) by referring to the decided type of the image segment in the search area "SA". Specifically, the step 106 decides the first solder portion 4 to be good (all correct, OK) when the type of the image segment in the search area "SA" agrees with one of the types "A", "B", and "C". The step 106 decides the first solder portion 4 to be no good (NG) when the type of the image segment in the search area "SA" agrees with one of the types "D", "E", and "F". When the first solder portion 4 is decided to be good (all correct, OK), the program advances from the step 106 to a step 107 of FIG. 30. Otherwise, the program advances from the step 106 to a step 108 of FIG. 30.

The step 107 of FIG. 30 sets an inspection result signal to a state corresponding to "OK". The step 107 stores the inspection result signal into the RAM 21 in relation to the information of the position of the first solder portion 4. After the step 107, the program advances to a step 111.

The step 108 of FIG. 30 sets an inspection result signal to a state corresponding to "NG". The step 108 stores the inspection result signal into the RAM 21 in relation to the information of the position of the first solder portion 4. After the step 108, the program advances to the step 111.

The step 109 of FIG. 30 stores the digital signal representative of the image segment in the search area "SA" into the second memory 16 as a digital signal representing a newly added reference image Rg.

A step 110 following the step 109 sets an inspection result signal to a state corresponding to "GRAY". The step 110 stores the inspection result signal into the RAM 21 in relation to the information of the position of the first solder portion 4. After the step 110, the program advances to the step 111.

The steps 104, 109, and 110 cooperate to execute the following processes. The image segment in the search area "A" is decided to be of none of the types "A", "B", "C", "D", "E", and "F" when the maximum matching rate is lower or smaller than 85%. Such an image segment in the search area "A" is decided to be gray (GRAY) intermediate between good (all correct, OK) and no good (NG). This image segment in the search area "A" is registered as a newly added reference image Rg corresponding to a newly added type "G" indicating "GRAY".

The step 111 decides whether or not all the solder portions 4 of the printed circuit board 1 have been inspected. In other words, the step 111 decides whether or not at least one solder portion 4 to be inspected remains. When at least one solder portion 4 to be inspected remains, the program returns from the step 111 to the step 101 of FIG. 29. As a result, second, third, and later ones of the solder portions 4 are inspected similarly to the previously-mentioned inspection of the first solder portion 4. It should be noted that second, third, and later ones of the solder portions 4 are inspected in response to the original reference images Ra, Rb, Rc, Rd, Re, and Rf and also the newly added reference image Rg. When all the solder portions 4 of the printed circuit board 1 have been inspected, the program advances from the step 111 to a step 112.

The step 112 controls the table controller 19 in response to the information of the position of first one of the NG solder portions 4 so that the actuators 6A for the table 6 are driven to locate the first NG solder portion 4 at a place near a position directly below the maker 12. The step 112 controls the marker controller 18 so that the cylinder 10 is activated and hence the marker 12 puts a red mark on a region of the printed circuit board 1 near the first NG solder portion 4. Then, similar locating and marking processes are executed for second and later ones of the NG solder portions 4. After the locating and marking processes have been completed for all the NG solder portions 4, the step 112 controls the table controller 19 in response to the information of the position of first one of the GRAY solder portions 4 so that the actuators 6A for the table 6 are driven to locate the first GRAY solder portion 4 at a place near a position directly below the marker 13. The step 112 controls the marker controller 18 so that the cylinder 11 is activated and hence the marker 13 puts a yellow mark on a region of the printed circuit board 1 near the first GRAY solder portion 4. Then, similar locating and marking processes are executed for second and later ones of the GRAY solder portions 4.

A step 113 following the step 112 checks whether at least one solder portion 4 decided to be gray (GRAY) is present or absent. When at least one solder portion 4 decided to be gray (GRAY) is present, the program advances from the step 113 to a step 114. Otherwise, the program exits from the step 113 before the current execution cycle of the program ends.

The step 114 activates the buzzer 31 so that the buzzer 31 generates sound for calling the user or operator. The operator visually inspects the GRAY solder portion (or portions) 4, and decides whether the GRAY solder portion 4 is good (all correct, OK) or no good (NG). It should be noted that the operator can easily find the GRAY solder portion 4 since a yellow mark is provided close thereto. The information of the position of the GRAY solder portion 4 may be indicated on a screen of the display portion 24. The step 114 informs the display portion 24 of the inspection result signal related to the GRAY solder portion 4, and controls the display portion 24 so that the inspection result signal related to the GRAY solder portion 4 is indicated on the screen of the display portion 24. The operator 23 actuates the input portion 23 while monitoring the screen of the display portion 24 so that the state of the inspection result signal related to the GRAY solder portion 4 is set to "OK" or "NG" according to the result of the visual inspection thereof. As a result, "OK" or "NG" is assigned to the newly added reference pattern Rg and the newly added type "G". After the step 114, the current execution cycle of the program ends.

The program of FIGS. 29 and 30 is executed once for inspecting each printed circuit board. After a newly added reference pattern Rg has been registered, the inspection of printed circuit boards is executed in response to the original reference patterns Ra–Rf and also the newly added reference pattern Rg.

What is claimed is:

1. A method of inspecting a solder portion, comprising the steps of:

obtaining an image of the solder portion;

collating the image of the solder portion with a plurality of predetermined reference patterns corresponding to different solder portion types respectively;

identifying a type of the solder portion in response to a result of the collating step; and deciding whether the solder portion is satisfactory or unsatisfactory in response to the identified type thereof.

2. The method of claim 1, wherein the collating step and the identifying step comprise calculating rates of matching of the image of the solder portion with the reference patterns respectively, selecting a maximum matching rate from among the calculated matching rates, and identifying the type of the solder portion as being equal to the type corresponding to the maximum matching rate.

3. A method of inspecting a solder portion, comprising the steps of:

obtaining an image of the solder portion;

calculating rates of matching of the image of the solder portion with predetermined reference patterns corresponding to different solder portion types respectively;

selecting a maximum matching rate from among the calculated matching rates;

comparing the maximum matching rate with a predetermined reference matching rate;

identifying a type of the solder portion as being equal to the type corresponding to the maximum matching rate when the maximum matching rate is greater than the reference matching rate; and deciding whether the solder portion is satisfactory or unsatisfactory in response to the identified type thereof.

4. The method of claim 3, further comprising the step of using the image of the solder portion as a new reference pattern corresponding to a new solder portion type when the maximum matching rate is equal to or smaller than the reference matching rate, the new solder portion type corresponding to a gray state between a satisfactory state and an unsatisfactory state.

5. An apparatus for inspecting a solder portion, comprising:

means for obtaining an image of the solder portion;

means for collating the image of the solder portion with a plurality of predetermined reference patterns corresponding to different solder portion types respectively;

means for identifying a type of the solder portion in response to a result of the collating by the collating means; and means for deciding whether the solder portion is satisfactory or unsatisfactory in response to the identified type thereof.

6. The apparatus of claim 5, wherein the collating means comprises a pattern matching circuit.

7. A method of inspecting a solder portion, comprising the steps of:

obtaining an image of the solder portion;

deciding which of predetermined reference patterns corresponding to different solder portion types respectively is most similar to the image of the solder portion, wherein each of the reference patterns corresponds to either a satisfactory solder portion state or an unsatisfactory solder portion state;

identifying a type of the solder portion as being equal to the type corresponding to the reference pattern most similar to the image of the solder pattern; and deciding whether the solder portion is satisfactory or unsatisfactory in response to the identified type thereof.

8. An apparatus for inspecting a solder portion, comprising:

means for obtaining an image of the solder portion;

means for deciding which of predetermined reference patterns corresponding to different solder portion types respectively is most similar to the image of the solder portion, wherein each of the reference patterns corresponds to either a satisfactory solder portion state or an unsatisfactory solder portion state;

means for identifying a type of the solder portion as being equal to the type corresponding to the reference pattern most similar to the image of the solder pattern; and means for deciding whether the solder portion is satisfactory or unsatisfactory in response to the identified type thereof.

* * * * *